(12) United States Patent
Melsheimer

(10) Patent No.: US 8,172,749 B2
(45) Date of Patent: May 8, 2012

(54) BOLSTER ASSEMBLY

(75) Inventor: Jeffry S. Melsheimer, Springville, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 569 days.

(21) Appl. No.: 11/859,874

(22) Filed: Sep. 24, 2007

(65) Prior Publication Data

US 2008/0082081 A1  Apr. 3, 2008

Related U.S. Application Data

(60) Provisional application No. 60/847,700, filed on Sep. 28, 2006.

(51) Int. Cl.
*A61B 1/00* (2006.01)
(52) U.S. Cl. ........................................ 600/184; 604/174
(58) Field of Classification Search .................. 600/184, 600/120; 604/174, 178, 175, 256, 257, 910, 604/27, 48, 524, 525, 526, 523, 270, 513, 604/264, 268; 606/108, 1; D24/112
See application file for complete search history.

(56) References Cited

U.S. PATENT DOCUMENTS

| | | | |
|---|---|---|---|
| 3,853,148 A * | 12/1974 | De Vincent et al. ........... 138/110 |
| 4,889,168 A * | 12/1989 | Kerzich et al. ................. 138/103 |
| 5,092,850 A | 3/1992 | Buma ........................... 604/175 |
| 5,267,968 A * | 12/1993 | Russo ........................... 604/174 |
| 5,267,969 A | 12/1993 | Hirsch et al. ................... 604/174 |
| 5,451,212 A | 9/1995 | Andersen ....................... 604/174 |
| 5,484,420 A * | 1/1996 | Russo ........................... 604/178 |
| 5,716,347 A | 2/1998 | Gibbs et al. .................... 604/247 |
| 5,720,734 A | 2/1998 | Copenhaver et al. ......... 604/247 |
| 6,030,361 A * | 2/2000 | Miyashiro ................... 604/96.01 |
| 6,808,519 B2 | 10/2004 | Fanelli et al. ................. 604/523 |
| 2002/0052576 A1* | 5/2002 | Massengale ............. 604/164.01 |
| 2003/0178086 A1* | 9/2003 | Hu ................................. 138/156 |
| 2008/0009831 A1* | 1/2008 | Griffin .......................... 604/531 |

* cited by examiner

*Primary Examiner* — Ryan Severson
*Assistant Examiner* — Tin Nguyen
(74) *Attorney, Agent, or Firm* — Brinks Hofer Gilson & Lione

(57) ABSTRACT

A bolster assembly for use in aligning a tubular interventional device along an outer epidermal layer of a patient. A base portion of the assembly has a first surface for contacting the epidermal layer at an exit site of the tubular interventional device from the body of the patient, and has a second surface generally opposite the first surface. An elongated member is engaged with the base portion second surface and extends therefrom at a first angle. The elongated member and the base portion are structured and aligned to define a passageway to enable passage therethrough of the tubular interventional device. The elongated member is capable of flexure relative to the base portion from the first angle to a second angle generally parallel to the epidermal layer. A retaining member is provided for releasably retaining the elongated member at the second angle.

16 Claims, 6 Drawing Sheets

FIG. 9
FIG. 10
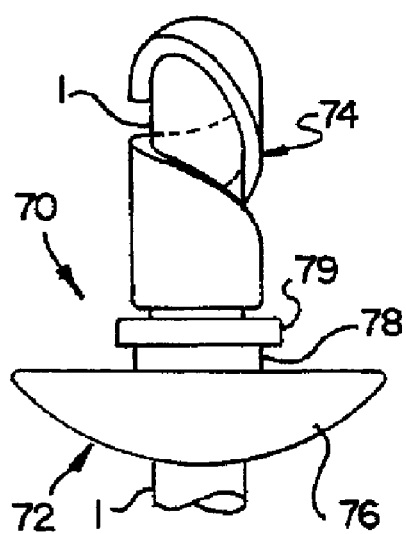
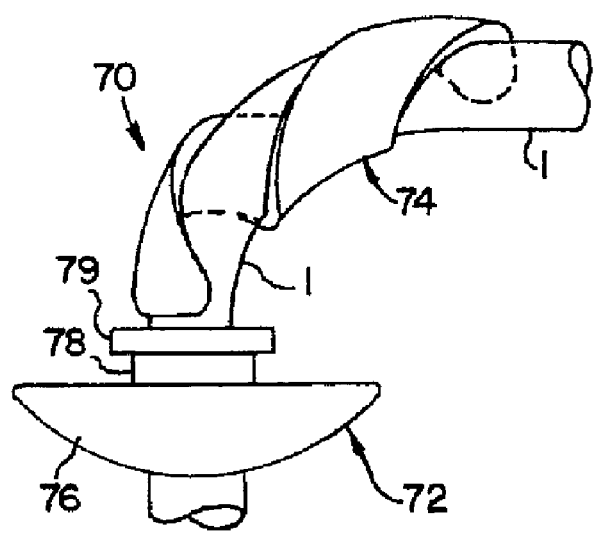
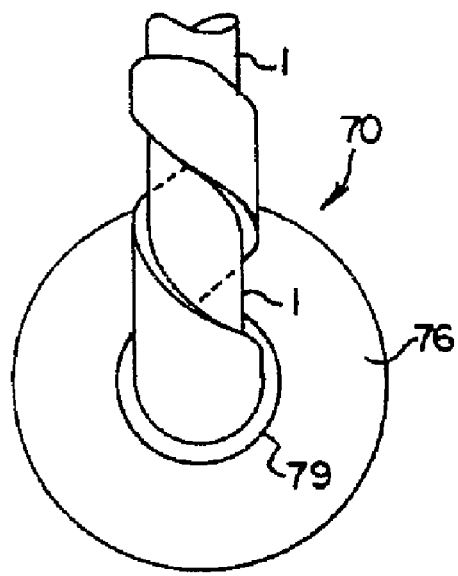
FIG. 11

BOLSTER ASSEMBLY

RELATED APPLICATION

The present patent document claims the benefit of the filing date under 35 U.S.C. §119(e) of Provisional U.S. Patent Application Ser. No. 60/847,700, filed Sep. 28, 2006, which is hereby incorporated by reference.

BACKGROUND

1. Technical Field

The present invention relates to medical devices, and more particularly, to a bolster assembly for maintaining a medical interventional device, such as a gastrostomy tube or a jejunostomy tube, in position along a body surface of a patient.

2. Background Information

Patients for whom normal ingestion of food becomes difficult or impossible may require placement of a feeding tube to assist in providing their nutritional needs. For some individuals, such as comatose patients, stroke victims, or those with a compromised gastrointestinal tract, this may require introduction of a feeding tube for delivery of nutritional products directly into the stomach or the jejunum. Tubes for delivery of nutritional products into the stomach are generally referred to as gastrostomy tubes, or "G"-tubes. Tubes for delivery of nutritional products into the jejunum are generally referred to as jejunostomy tubes, or "J"-tubes. In many cases in which a J-tube is utilized, the J-tube is inserted through the interior of a previously positioned G-tube.

There are two general methods for percutaneously positioning a gastrostomy tube in a patient. One such method, referred to as the Ponsky, or "pull", method involves introduction of an endoscope through the patient's mouth and esophagus and into the stomach. The endoscope contains a light source having sufficient power such that the position of the endoscope can be visualized on the outside of the patient's abdomen. A needle is then inserted through the abdominal wall and is visualized by the endoscope. A wire guide is passed through the needle and is grasped by the endoscope and pulled up through the esophagus and out through the mouth. The wire guide is then fastened to the end of the gastrostomy tube, and pulled back down through the esophagus and stomach. The leading end of the wire guide and the external portion of the gastrostomy tube are pulled out through the aperture in the abdominal wall initially formed by the needle. Typically, an internal bolster, such as a balloon, is provided internal of the stomach to hold the stomach against the abdominal wall, and an external bolster is provided external of the abdomen for anchoring the device exterior of the patients skin.

The other method is commonly referred to as the "push" method. In this method, the endoscope is used to provide the physician with a visual indication of the stomach, and a needle and wire guide are inserted into the stomach through the abdominal wall utilizing, e.g., the well-known Seldinger percutaneous-entry technique. In this technique, following withdrawal of the needle, the physician inserts, or pushes, the gastrostomy tube through the abdominal wall over the wire. The tube may be anchored with internal and external bolsters in the manner described above. Following placement via either of these two methods, proper positioning of the internal bolster against the stomach wall may be confirmed with the endoscope.

Feeding tubes used in long-term enteral feeding are generally made from an inert, biocompatible medical grade material such as silicone rubber or polyurethane. Such tubes are generally soft and flexible, so that they do not cause undue discomfort to the patient. In an attempt to eliminate the discomfort and inconvenience of a perpendicularly-extending tube, such tubes are often flexed over at a right angle, in a manner such that the tube is taped down on the skin surface. One problem with this arrangement is that such tubes have a tendency to kink at the point where the tube is flexed over at the right angle. Repeated flexing of the tube at the juncture as it exits the bolster creates continuous stress at the flexure point. This action weakens the tube, and increases the possibility that stress fractures and cracking of the tube wall may occur, which actions may lead to premature failure of the device. This is especially true in smaller diameter tubes, such as the 18 French, or smaller, tubes used with pediatric patients. These smaller size tubes often also have thinner walls, which makes them even more susceptible to premature failure from repeated flexing of the tube. In addition, when tape is utilized to tape the tube to the skin surface, the removal of the tape tends to leave a residue on the skin of the patient. Such tape is also difficult to clean, painful to remove, and erosive to the skin.

It would be desired to provide an external bolster assembly for an interventional medical device that overcomes the problems of prior art devices.

BRIEF SUMMARY

The present invention addresses the shortcomings of the prior art. In one form thereof, the present invention comprises a bolster assembly for use in aligning a tubular interventional device along an outer epidermal layer of a patient. A base portion of the assembly has a first surface for contacting the epidermal layer at an exit site of the tubular interventional device from the body of the patient, and has a second surface generally opposite the first surface. An elongated portion of the assembly is engaged with the base portion second surface and extends therefrom at a first angle. The elongated portion and the base portion are structured and aligned to define a passageway to enable passage therethrough of the tubular interventional device. The elongated portion is capable of flexure relative to the base portion from the first angle to a second angle generally parallel to the epidermal layer. A retaining member is provided for releasably retaining the elongated portion at the second angle.

In another form thereof, the present invention comprises a bolster assembly for use in aligning a tubular interventional device along an outer epidermal layer of a patient. The bolster assembly comprises a base portion having a first surface for contacting the epidermal layer at an exit site of the interventional device from the body of the patient, and having a second surface. The base portion further has a longitudinal passageway extending therethrough. An elongated portion of the assembly has a first end and a second end. The first end is engaged with the base portion second surface such that the elongated portion extends therefrom. The elongated portion has a longitudinal passageway extending therethrough aligned with the base portion longitudinal passageway for passage of the interventional device. The elongated portion is structured such that the second end is angularly offset relative to the first end such that the interventional device is alignable generally parallel to the epidermal layer.

In yet another form thereof, the present invention comprises a bolster assembly for use in aligning a tubular interventional device along an outer epidermal layer of a patient. A base portion of the assembly has a first surface for contacting the epidermal layer at an exit site of the interventional device from the body of the patient, and has a second surface.

The base portion further includes a longitudinal passageway extending therethrough. An elongated guide portion of the assembly has a first end, a second end, and a longitudinal passageway extending therethrough. The elongated guide portion first end is alignable with the base portion second surface such that the elongated guide portion is extendable therefrom at a first angle. The elongated guide portion longitudinal passageway is alignable with the base portion longitudinal passageway for passage of the interventional device. The elongated guide portion is capable of flexure relative to the base portion from the first angle to a second angle generally parallel to the epidermal layer. The guide portion has a stiffness greater than or equal to the stiffness of the interventional device, such that upon flexure of the guide portion to the second angle, the interventional device is maintained at the second angle.

BRIEF DESCRIPTION OF THE DRAWINGS

FIGS. 1A-1D illustrate the separate features of the external bolster assembly of FIG. 1;

FIG. 9 is an end view of the bolster assembly utilizing the components of FIGS. 7 and 8, and illustrating a gastrostomy tube received in a passageway of the bolster assembly;

FIG. 10 is a side view of the bolster assembly and gastrostomy tube of FIG. 9; and FIG. 11 is a top view of the bolster assembly and gastrostomy tube of FIG. 10.

DETAILED DESCRIPTION OF THE DRAWINGS AND THE PRESENTLY PREFERRED EMBODIMENTS

Figure 1:
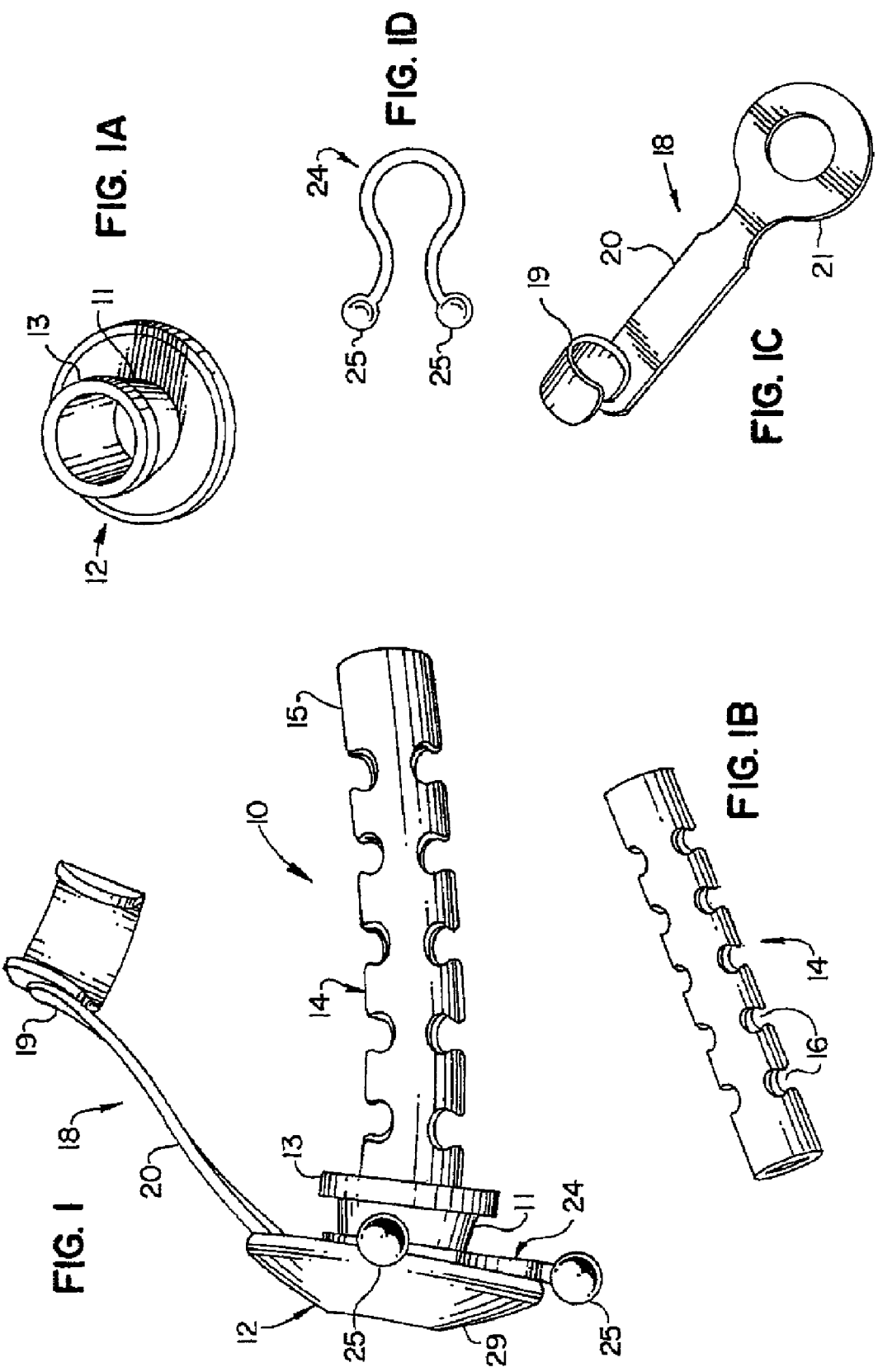
FIG. 1 is a side view of an external bolster assembly according to an embodiment of the present invention.

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive assembly, as well as the axial ends of various component features. The term "proximal" is used in its conventional sense to refer to the end of the assembly (or component thereof) that is closest to the operator during use of the assembly. The term "distal" is used in its conventional sense to refer to the end of the assembly (or component thereof) that is initially inserted into the patient, or that is closest to the patient during use.

Figure 2:
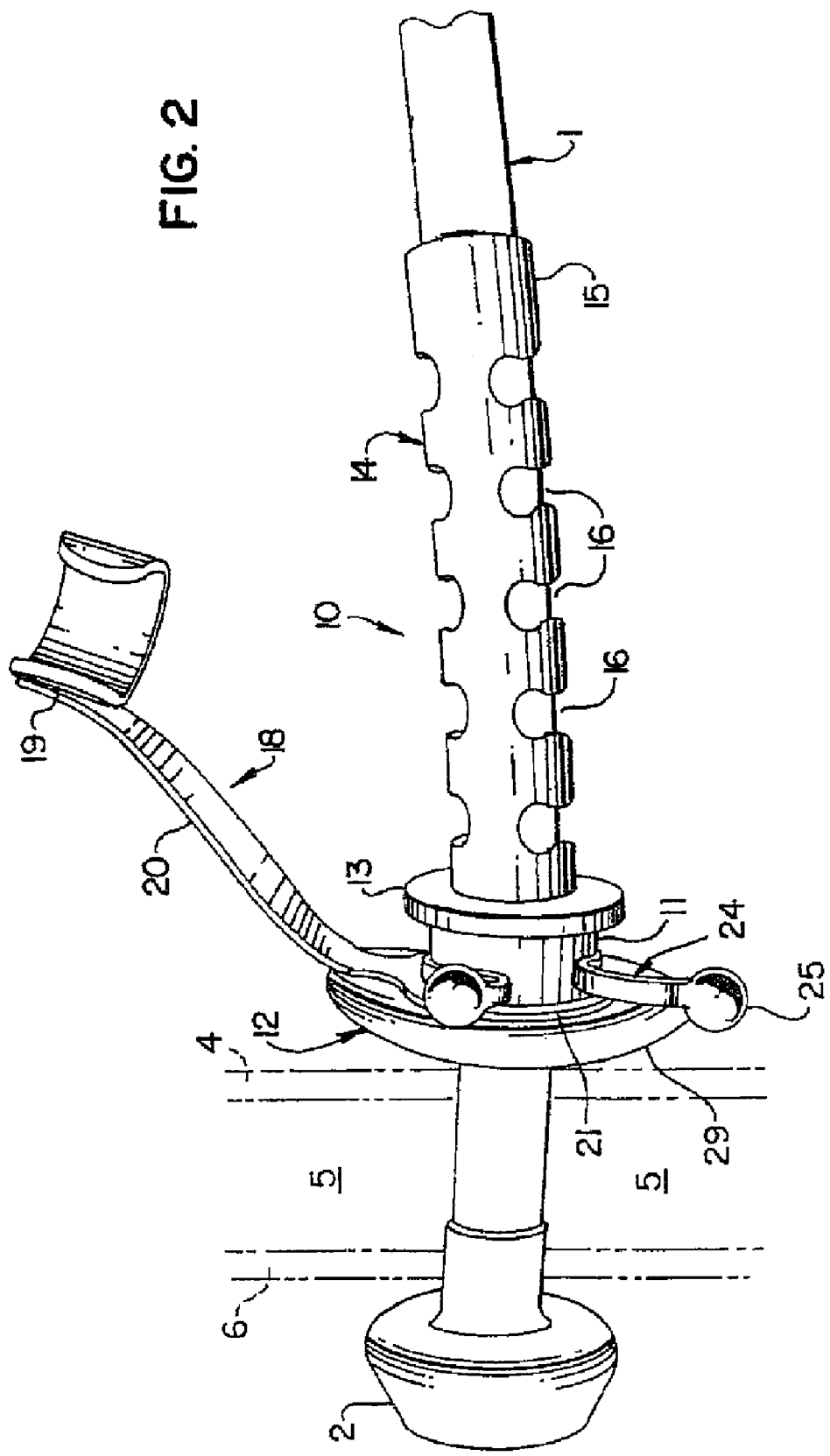
FIG. 2 is a side view of the external bolster assembly of FIG. 1 in cooperating relationship with a gastrostomy tube.

FIG. 1 illustrates an external bolster assembly 10 according to an embodiment of the present invention. FIGS. 1A-1D illustrate the separate elements of the preferred embodiment of the bolster assembly shown in FIG. 1. FIG. 2 illustrates external bolster assembly 10 in cooperating relationship with a medical interventional device of the type that extends from the exterior of the patient to a site internal of the patient. In the non-limiting example illustrated herein, the medical interventional device comprises an enteral feeding tube 1, such as a conventional gastrostomy, or "G", tube. In the embodiment shown, bolster assembly 10 includes a base portion 12, an elongated body portion 14, and a retaining portion, such as grasping member 18. An optional securing structure, such as twist lock member 24, may be provided for applying a gripping pressure on the feeding tube.

Preferably, base portion 12 comprises the dome-like configuration 29 shown in the figures. Utilizing a dome-like configuration at the distal portion of the base that contacts the skin of the patient provides the bolster with a limited ability to rock back and forth upon movement of the gastrostomy tube, which rocking movement causes only minimal, if any, trauma to the skin of the patient. In the non-limiting example shown, base portion 12 includes a collar portion 11 proximal to dome-shaped portion 29, and a retaining flange 13 proximal to the collar.

Elongated body portion 14 preferably includes a plurality of cut-outs, or slots, 16 disposed along its length. Slots 16 lend bilateral flexibility to elongated body portion 14, thereby inhibiting kinking of the gastrostomy tube, while at the same time allowing the body portion to retain circumferential stiffness between the slots. Any number and configuration of slots can be provided along body portion 14, with the number and configuration of slots shown in the drawings being merely one possible arrangement.

Grasping member 18 may extend from base portion 12 (as shown in the figures), or from a distal segment of elongated body portion 14. Grasping member 18 comprises a grasping element 19 disposed at an end of elastomeric band 20. Ring 21, or analogous engagement structure, is preferably disposed at the opposite end of band 20 for engaging grasping member 18 with base portion 12, most preferably at base portion collar 11. Grasping element 19 is sized and shaped for selectively receiving and retaining a segment of body portion 14, in a manner to be described.

Preferably, bolster assembly 10 also includes a twist lock member 24 for applying a gripping pressure on the feeding tube. Twist lock member 24 includes ends 25 that are selectively twistable around collar 11 to apply a gripping pressure on an enteral feeding tube, such as gastrostomy tube 1 (FIG. 2), for inhibiting movement of the tube when the tube is positioned within a longitudinal passageway extending through bolster assembly 10.

The use of enteral feeding tubes, such as gastrostomy tubes and jejunostomy tubes, for transmitting nutritional products from a site external of the patients body to a site within the stomach or jejunum of the patient is well known in the medical arts. Such tubes are generally formed of a bendable polymeric material such as silicone, polyurethane, a copolymer of silicone and polyurethane, or a polyamide, such as nylon. Typically, an internal member, such as a balloon or a flared portion of the tube, is provided at a portion of the gastrostomy tube positioned internal of the stomach to hold the anterior stomach wall against the abdominal wall. An external bolster is typically provided external of the patient for anchoring the device exterior of the patient's skin. The use of bolsters to anchor a feeding tube is also well known in the art.

FIG. 2 schematically illustrates the relative position of gastrostomy tube 1 and external bolster assembly 10 when the tube is inserted through an opening in the abdominal wall of a patient and into the stomach. As illustrated, the distal end of tube 1 extends through epidermal surface 4, abdominal wall 5 and stomach wall or lining 6. Internal member 2 is one example of the type of internal bolster commonly used with feeding tubes that are inserted through the mouth via the pull method described above. When the push method is utilized, the internal member may typically comprise an inflatable balloon or a pig-tail structure. In either event, the internal bolster is positioned to abut the inner surface of stomach wall 6. Base portion 12 is positioned in a manner such that it abuts, or substantially abuts, the external epidermal surface 4.

Although placement of a gastrostomy tube in the manner shown in FIG. 2 would provide an efficient passageway for nutritional products to pass through tube I from an external food source into the stomach, the presence of the feeding tube extending in a perpendicular direction from the epidermal surface 4 as shown in FIG. 2 would cause inconvenience to many patients. Therefore, it is desired to provide a mechanism that is capable of providing, and maintaining, a low profile to the feeding tube relative to the epidermal surface.

Figure 3:
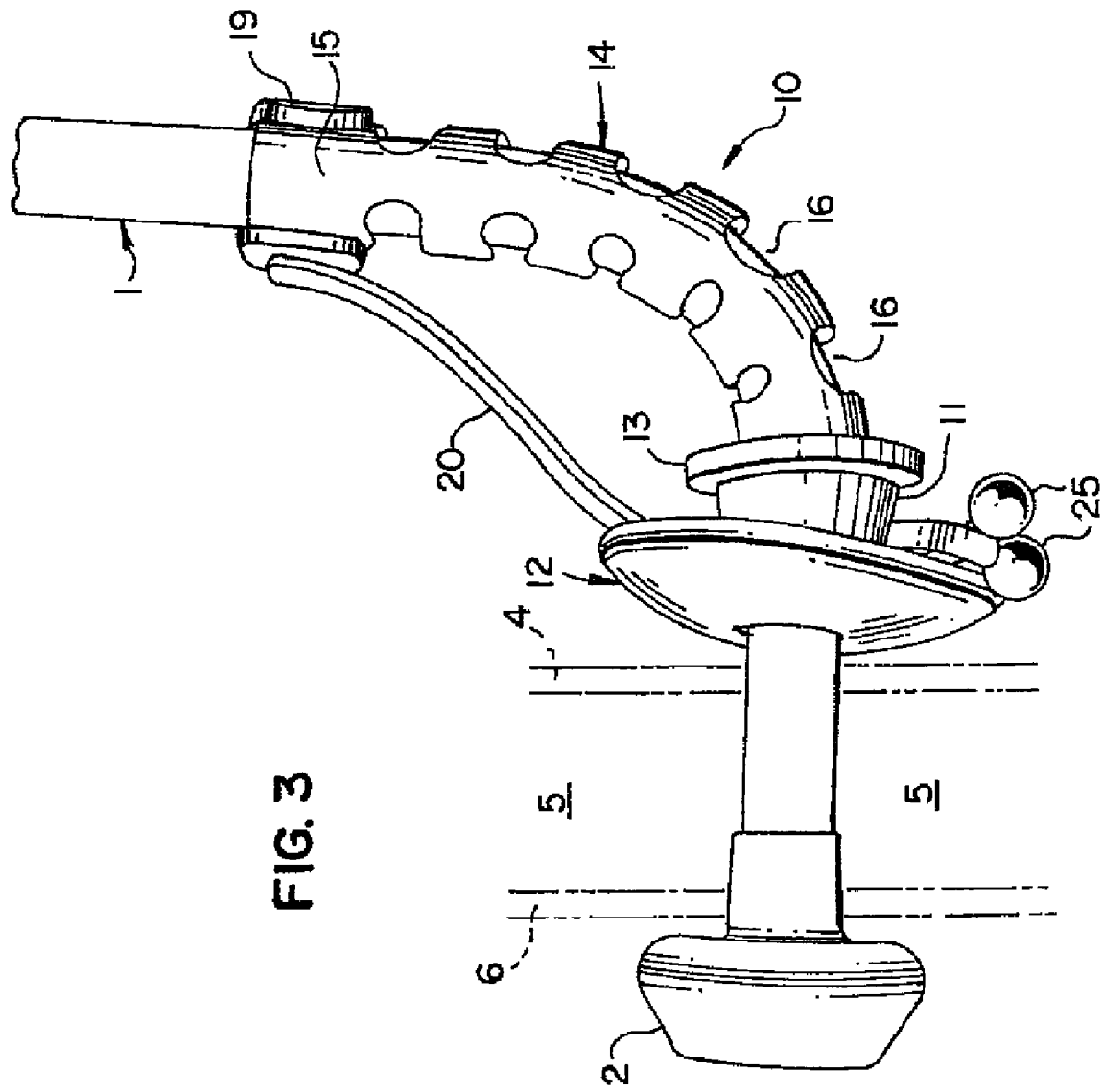
FIG. 3 is a side view of the bolster assembly and gastrostomy tube of FIG. 2 wherein the gastrostomy tube is oriented parallel to the epidermal surface of a patient.

The use of bolster assembly 10 enables gastrostomy tube 1 to be oriented in a manner such that tube I is parallel, or substantially parallel, to the outer epidermal surface 4. In this manner, the outwardly extending profile of the tube is considerably reduced when compared to the perpendicular orientation shown in FIG. 2. This arrangement is shown in FIG. 3. To effect the desired orientation of tube 1, band 20 is sized and positioned such that grasping element 19 may releasably capture a proximal end 15 of elongated body portion 14. As a result, the perpendicular orientation of tube 1 as shown in FIG. 2 is converted to a parallel orientation (relative to the epidermal layer) as shown in FIG. 3. Thus, when properly positioned, the length of tube 1 is substantially adjacent a length of the epidermal layer.

Preferably, the components of bolster assembly 10 are formed of a relatively flexible polymeric or elastomeric material, such as silicone rubber, polyurethane, or a co-polymer of each. All portions of bolster assembly 10 need not necessarily be formed from the same composition, and the durometers of the various segments need not necessarily be the same. In most cases, the durometer of the elements of the bolster will be higher than the durometer of the feeding tube. Grasping element 19 is sized and configured such that the proximal end 15 of bolster body member 14 is releasably received therein. Grasping element 19 and bolster proximal end 15 are cooperatively sized and shaped to cause proximal end 15 to remain "locked" in the position shown in FIG. 3 until such time as it is desired to remove, or alter, the position of the gastrostomy tube. At this time, proximal end 15 may simply be removed from within grasping member by unsnapping or other removal means.

The various portions of external bolster assembly 10 may be formed by well-known methods, such as injection molding or casting. Slots 16 may be cut or molded/cast into body portion 14 by well-known means.

Figure 4:
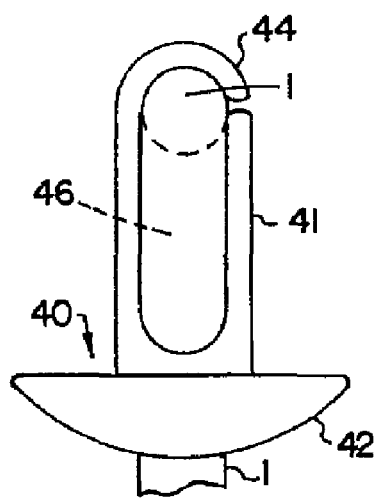
FIG. 4 is an end view of another embodiment of an external bolster assembly, illustrating a gastrostomy tube received in a passageway of the bolster assembly.
Figure 5:
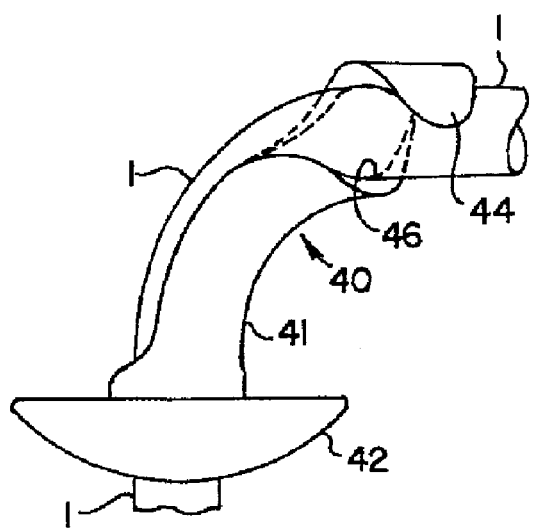
FIG. 5 is side view of the bolster assembly and gastrostomy tube of FIG. 4.
Figure 6:
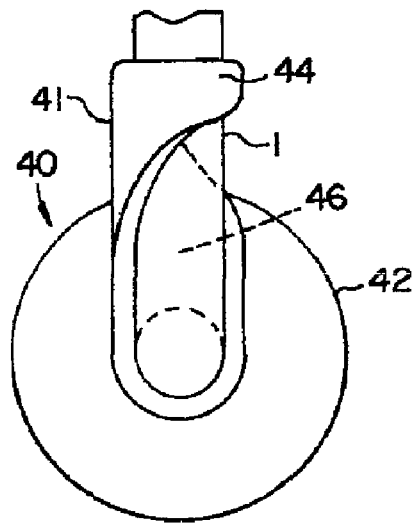
FIG. 6 is a top view of the bolster assembly and gastrostomy tube of FIG. 4.
Figure 7:
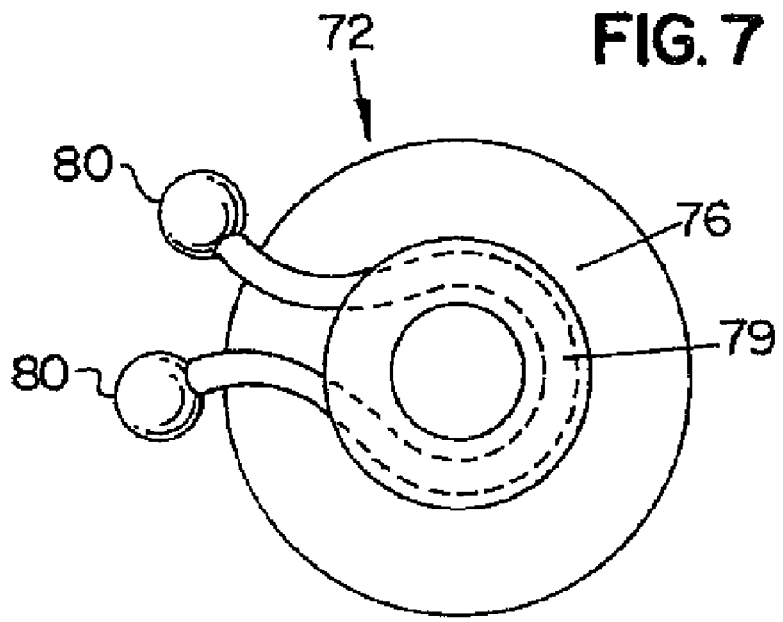
FIGS. 7 and 8 illustrate the components of a bolster assembly according to yet another embodiment of the present invention.
Figure 8:
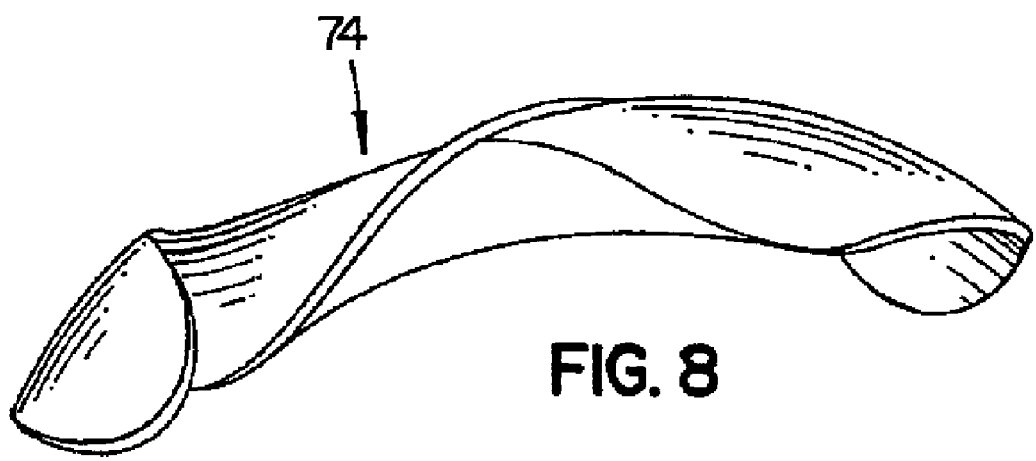

FIGS. 4-6 illustrate respective end, side and top views of another embodiment of an external bolster assembly 40 for use with a medical interventional device. In each of FIGS. 4-6, a gastrostomy tube 1 is shown received in a passageway 46 of the bolster. Bolster assembly 40 comprises an elongated body 41 formed, e.g., of silicone, polyurethane, a copolymer of silicone and polyurethane, or nylon, and a base portion 42 disposed at the distal end of elongated body 41. Preferably, base portion 42 is dome-shaped as shown in the figures. Passageway 46 extends through bolster assembly 40 for receiving a conventional gastrostomy tube 1. A retaining tab 44 is provided at the proximal end of bolster assembly 40 for retaining gastrostomy tube 1 in a flexed position. The positioning of retaining tab 44 for maintaining flexure of tube 1 is best shown in FIG. 5. Preferably, bolster assembly 40 is molded or cast as an integral assembly.

As illustrated, bolster assembly 40 is sized and shaped to cause gastrostomy tube 1 to be flexed, or bent, in a manner such that it is substantially parallel to the epidermal layer of a patient, in a manner similar to that of the gastrostomy tube shown in FIG. 3. In order to have sufficient structural strength and integrity to flex the gastrostomy tube, and to maintain it in the flexed positioned shown in the figures, it is important that that at least one of the base portion 42 and elongated body 41, and preferably the elongated body 41, have a higher stiffness than the stiffness of the gastrostomy tube. If desired, bolster assembly 40 may also be provided with a collar portion and removable twist lock members as shown in the embodiment of FIGS. 1-3 for applying a gripping pressure on the gastrostomy tube 1.

Yet another embodiment of the present invention comprises the bolster assembly shown in FIGS. 7-11. In this embodiment, the bolster assembly 70 comprises an initially separate distal member 72 and proximal elongated member 74. Distal member 72 may comprise an external bolster of a type known in the art. In the non-limiting example shown, the external bolster has a dome-shaped portion 76, a collar portion 78 proximal to dome-shaped portion 76, and a retaining flange 79 proximal to the collar. Optional removable twist lock members 80 (FIG. 7) may be provided for selectively twisting members 80 around collar 78 to apply a gripping pressure on a gastrostomy tube 1, in the manner described previously. Distal member 72 is preferably formed of an elastomeric composition, such as silicone rubber or polyurethane, a copolymer formed of silicone and polyurethane, or nylon.

Proximal elongated member 74 comprises a tubular guide. Preferably, the tubular guide may be spirally wrapped in the general nature of a helix. This is best shown in FIG. 10. Elongated member 74 is preferably formed of a rigid or semi-rigid material, such as polyurethane. The elongated member is capable of flexure relative to the base portion from a first angle, such as perpendicular to the epidermal layer, to a second angle generally parallel to the epidermal layer. Flexure of the elongated member to the second angle is also best shown in FIG. 10. The stiffness of the guide member 74 should be at least as great as, and preferably greater, than the stiffness of the interventional device. As a result, when the elongated member is flexed to the second angle, the interventional device is also maintained at the second angle, and cannot spring back to the first angle or any intermediate angle. Although the elongated guide member may also be formed of silicone and other elastomeric compositions in a particular case, it is important that the guide member be formed of a composition having sufficient strength and stiffness to maintain gastrostomy tube 1 in the flexed position shown in FIG. 10. Elongated member 74 may be molded, cast, or formed by other known means that are capable of imparting the configuration and the bend shown in the figures.

As shown in FIGS. 7-11, dome member 72 and elongated member 74 are initially separate structures that are combinable to form bolster 70. Following insertion of the feeding tube by conventional means, dome member 72 is slid over the tube until it abuts, or substantially abuts, the outer epidermal layer of the patient. Elongated member 74 is then slid over the tube in twisting fashion immediately proximal to the dome member 72. Alternatively, elongated member 74 can be simply wrapped around the tube. As another alternative, the elongated member may be "side-loaded" onto the feeding tube, without having to slide it on from an end.

In an alternative embodiment, dome member 72 and elongated member 74 of the bolster assembly need not necessarily be initially separate structures as described. Rather, these components may comprise an integral structure. However, by maintaining separate structures, elongated member 74 may in some instances be used in combination with an existing external bolster that has been previously placed and utilized, thereby providing freedom of placement, tension, direction, etc.

The inventive bolster assemblies as described herein require no additional fixturing to the patient when compared to prior art bolsters. In the preferred embodiments disclosed, the bolster assemblies may be formed separately or as an integral unit, and the segments of the assembly may be formed of the same, or a similar, composition.

Once inserted, the inventive bolster assembly forms a compatible radius with the feeding tube, and is preferably structured such that the bend of the tube is visible. As a result, any kinking, bending, pinching, bulging, etc., of the tube is also visible, thereby permitting corrective action to be immediately taken. In addition, the bolster assembly is formed from a composition (or compositions) that is compliant under the type of compression exerted when it is used to bend the feeding tube. As a result, it does not cause pressure to be exerted against the abdomen when applied to the tube. The inventive bolster assemblies are structured such that they do not hinder the functionality of the feeding tube.

Although the bolster assembly is shown bending the feeding tube in a first direction (e.g., right) as shown in FIGS. 5 and 10, those skilled in the art will appreciate that the assembly can alternatively be arranged to bend the tube in other directions, such as a second (e.g., left) direction. In addition, with the inventive bolster assembly, the feeding tube need not be taped to the skin as with prior art bolsters. This eliminates a potential source of discomfort and irritation to the patient, particularly upon removal of the tape. Furthermore, the bolster assembly is easy to remove and clean, and allows easy removal of the feeding tube for removal and cleaning. Finally, a bolster assembly may be sized to enable it to accommodate a wide variety of sizes of feeding tubes. Thus, for example, it may only be necessary for a medical institution to maintain two sizes of bolster assemblies; one for use with adult, or large, patients, and another for use with small, or pediatric, patients.

While these features have been disclosed in connection with the illustrated preferred embodiments, other embodiments of the invention will be apparent to those skilled in the art that come within the spirit of the invention as defined in the following claims.

The invention claimed is:

1. A bolster assembly for use in aligning a tubular interventional device along an outer epidermal layer of a patient, the bolster assembly comprising:
   a base portion, said base portion having a first surface for contacting said epidermal layer at an exit site of said tubular interventional device from the body of the patient, and having a second surface;
   an elongated portion having a proximal end and a distal end, said distal end engaged with said base portion second surface such that said elongated portion extends therefrom at a first angle generally perpendicular to said epidermal layer, said elongated portion and said base portion structured and aligned such that said portions define a passageway for passage therethrough of said tubular interventional device, said elongated portion having a plurality of slots disposed along a length thereof for imparting a flexibility thereto, such that said elongated portion flexes between said first angle and a second angle generally parallel to said epidermal layer, said elongated portion positioned substantially adjacent a length of the epidermal layer at said second angle for minimizing an outwardly extending profile thereof; and
   a retaining member having first and second ends, said first end extending from one of said base portion and the distal end of said elongated portion, and said second end including a grasping mechanism, said grasping mechanism structured and arranged for selectively capturing a surface of said elongated portion proximal end for maintaining said profile at said second angle and for selectively releasing said surface to achieve said first angle.

2. The bolster assembly of claim 1, wherein said base portion first surface is generally dome-shaped.

3. The bolster assembly of claim 1, wherein a durometer of at least one of said base portion and said elongated portion exceeds a durometer of said interventional device.

4. The bolster assembly of claim 1, wherein said retaining member comprises an elastomeric band, and wherein said first end of said retaining member extends from said base portion.

5. The bolster assembly of claim 1, wherein said retaining member comprises an elastomeric band.

6. The bolster assembly of claim 5, further comprising a ring for engaging said retaining member with said base portion.

7. The bolster assembly of claim 1, wherein at least one of the base portion and elongated portion is formed from a member selected from the group consisting of polyurethane, silicone, copolymers of polyurethane and silicone, and a polyamide.

8. The bolster assembly of claim 1, wherein said base portion second surface comprises a retaining flange.

9. The bolster assembly of claim 8, wherein said base portion further comprises a collar intermediate said first and second surfaces, said assembly further comprising a twist lock member sized and positioned along said collar portion for applying a gripping pressure on said interventional device.

10. The bolster assembly of claim 9, further comprising a ring for engaging said retaining member with said base portion collar.

11. The bolster assembly of claim 1, wherein said base portion first surface is generally dome-shaped, and wherein said retaining member first and second ends are engaged by an elastomeric band, said first end extending from said base portion.

12. A bolster assembly for use in aligning a tubular interventional device along an outer epidermal layer of a patient, comprising:
   a base portion, said base portion having a first surface for contacting said epidermal layer at an exit site of said interventional device from the body of the patient, and having a second surface, said base portion further having a longitudinal passageway extending therethrough;
   an elongated portion having a distal end and a proximal end, said distal end engaged with said base portion second surface such that said elongated portion extends therefrom, said elongated portion having a longitudinal passageway extending therethrough aligned with said base portion longitudinal passageway for passage of said interventional device, said elongated portion having a flexibility such that said proximal end of said elongated portion is movable relative to said distal end, said proximal end movable between a first position generally perpendicular to said epidermal layer and a second position generally parallel to said epidermal layer; and a retaining member having first and second ends, said first end extending from one of said base portion and the distal end of said elongated portion, and said second end including a grasping mechanism, said grasping mechanism structured and arranged for selectively capturing a surface of said elongated portion proximal end for maintaining said second position, and for selectively releasing said surface to achieve said first position.

13. The bolster assembly of claim 12, wherein the elongated portion has a stiffness that exceeds a stiffness of the interventional device, and wherein said elongated portion includes a plurality of slots disposed between said first and second ends.

14. The bolster assembly of claim 12, wherein said base portion first surface is generally dome-shaped.

15. The bolster assembly of claim 12, wherein said base portion and said elongated portion comprise an integral structure, and wherein said elongated portion includes a plurality of slots disposed between said first and second ends in a manner to impart bilateral flexibility to the elongated portion.

16. The bolster assembly of claim 12, wherein at least one of the base portion and elongated portion is formed from a member selected from the group consisting of polyurethane, silicone, copolymers of polyurethane and silicone, and a polyamide.

* * * * *